(12) United States Patent
Sauer et al.

(10) Patent No.: US 8,066,803 B2
(45) Date of Patent: Nov. 29, 2011

(54) VACUUM CLEANER FILTER BAG

(75) Inventors: Ralf Sauer, Overpelt (BE); Jan Schultink, Overpelt (BE)

(73) Assignee: Eurofilters Holding N.V., Overpelt (BE)

( * ) Notice: Subject to any disclaimer, the term of this patent is extended or adjusted under 35 U.S.C. 154(b) by 723 days.

(21) Appl. No.: 11/934,179

(22) Filed: Nov. 2, 2007

(65) Prior Publication Data

US 2008/0115671 A1    May 22, 2008

(30) Foreign Application Priority Data

Nov. 3, 2006 (EP) .................................... 06022951

(51) Int. Cl.
*B01D 46/02* (2006.01)

(52) U.S. Cl. ........... 96/223; 55/DIG. 2; 55/382; 55/486; 96/226

(58) Field of Classification Search .............. 55/385.1, 55/DIG. 2, DIG. 5; 96/226
See application file for complete search history.

(56) References Cited

U.S. PATENT DOCUMENTS

| | | | | |
|---|---|---|---|---|
| 6,063,171 A | * | 5/2000 | Moyher et al. | 96/226 |
| 6,156,086 A | * | 12/2000 | Zhang | 55/382 |
| 6,372,004 B1 | * | 4/2002 | Schultink et al. | 55/382 |
| 6,395,046 B1 | * | 5/2002 | Emig et al. | 55/382 |
| 6,706,086 B2 | * | 3/2004 | Emig et al. | 55/486 |

FOREIGN PATENT DOCUMENTS

| | | |
|---|---|---|
| DE | 29 11 004 A1 | 10/1980 |
| DE | 20 2005 012 846 U1 | 1/2005 |
| DE | 20 2005 009 452 U1 | 9/2005 |
| DE | 10 2006 016 009 A1 | 1/2008 |
| EP | 0 960 645 A2 | 12/1999 |
| EP | 1 310 288 A1 | 5/2003 |
| JP | 2009-155125 * | 6/1997 |
| JP | 2000-041919 * | 2/2000 |
| JP | 2005-126871 A | 5/2005 |
| JP | 2005 161308 A | 6/2005 |
| JP | 2006-169152 * | 6/2006 |
| WO | WO 00/06210 A1 | 2/2000 |
| WO | WO 2005/060807 A1 | 7/2005 |

* cited by examiner

*Primary Examiner* — Duane Smith
*Assistant Examiner* — Sonji Turner
(74) *Attorney, Agent, or Firm* — Brinks Hofer Gilson & Lione

(57) ABSTRACT

The invention relates to vacuum cleaner filter bag with a bag wall made of a filter material, wherein the bag wall and/or the interior of the vacuum cleaner filter bag comprise fibres containing a biopolymer and having an antibacterial effect and/or a powder produced from a biopolymer and having an antibacterial effect.

22 Claims, 2 Drawing Sheets

VACUUM CLEANER FILTER BAG

TECHNICAL FIELD

The invention relates to a vacuum cleaner filter bag with particularly improved hygienic characteristics.

BACKGROUND

In the manufacture of vacuum cleaner filter bags that are inserted into a vacuum cleaner and that are intended to hold the dust that is suctioned in, one of the main focuses of the development is to increase the dust-holding capacity and service life. To accomplish these, there are different approaches that concern the filter structure, i.e., the configuration of the filter material layers of the bag wall and/or the parameters of the individual layers themselves.

For example, EP 0 960 645 exhibits a multi-layer filter configuration in which a coarse filter layer is arranged before a fine filter layer, as seen in the direction of flow. In particular, larger quantities of dust are intended to be deposited in the coarse filter layer, which prevents the entire filter structure from becoming quickly blocked.

A further possibility is defined in WO 2005/060807, according to which a vacuum cleaner filter bag contains a material that can be swirled around in the presence of a given air flow.

From DE 10 2006 016 009, a vacuum cleaner filter bag with a deflective device is known by means of which the service life can likewise be significantly increased.

Another focus during the enhancement of vacuum cleaner filter bags consists of the suppression of the formation of unpleasant smells and/or bacteria growth for reasons of hygiene. In this connection, DE 20 2005 009 452 describes a vacuum cleaner bag, whereby one of the items arranged inside is a biocide. In particular, plant parts+powders of, e.g., chamomile, thyme or oregano are mentioned for this. Complete plant parts are not fibrous by nature and cannot be processed into nonwovens. In addition to active components, plant parts also contain high proportions of builders that reduce the effectiveness (dilution effect).

Known from DE 29 11 004 is a filter bag which has a coating with a nonwoven on its interior side, whereby said nonwoven is provided with antimycotic or antibacterial agents. Various synthetic substances are used thereby as antibacterial and antimycotic agents.

The disadvantage of a filter bag of this type lies in the fact that the use of synthetic bactericides and fungicides is ecologically and economically problematic. The active substances are expensive and frequently cause allergic reactions. The manufacturing processes for the filter bag are further complicated by the additional layer, and the filter characteristics of the filter bag also change unpredictably, because, in particular, the oily biocides can influence the characteristics of the successive filter layers. For example, the persistence of an electrostatic charge of a nonwoven is reduced by contact with oily substances.

SUMMARY OF THE INVENTION

An object of the present invention consequently includes overcoming the abovementioned disadvantages of the state of the art and providing a vacuum cleaner filter bag, with improved hygiene, that can be produced in a simple manner.

According to the invention, a vacuum cleaner filter bag is provided with a bag wall made of filter material, whereby in the bag wall and/or in the interior of the vacuum cleaner finer bag, fibres comprising a biopolymer and having an antibacterial effect and/or a powder, produced from a biopolymer and having an antibacterial and/or fungicidal effect is provided.

Biopolymers are understood as macromolecules that occur in living (particularly plant or animal) organisms or that are produced from these. Examples of biopolymers are proteins, peptides, polysaccharides, such as cellulose, or polyaminosaccharides, such as chitosan.

The fibres can be chemical fibres made of natural or synthetic polymers or natural fibres (particularly plant fibres). These terms are used here and in the following in accordance with W. Albrecht et al., *Nonwoven Fabrics*, Wiley-VCH, 2000.

Chemical fibres made of natural polymers are particularly obtained from solutions by means of regeneration; in this way, cellulosic chemical fibres (cellulose fibres) are obtained from solutions of cellulose or cellulose derivatives by means of regeneration. Chemical fibres can be formed as staple fibres or continuous fibres (filaments).

Natural fibres comprise plant and animal fibres that do not run through any regeneration step. Possible natural fibres are, for example, cellulose fibres that occur in cellulose from coniferous wood or bamboo. In the following, natural fibres are meant when there are references to cellulose or pulp fibres (for example, bamboo pulp fibres). The term staple fibres, on the other hand, describes a form of chemical fibres; bamboo staple fibres are, for example, obtained from solutions of bamboo pulp or bamboo pulp derivatives through regeneration of cellulose fibres.

Consequently, particularly the bag wall and/or the interior of the vacuum cleaner filter bag can contain, for example, staple fibres that comprise a biopolymer with antibacterial effect.

In the following, the phrase "antibacterial fibres" is sometimes used synonymously instead of the phrase "fibres comprising a biopolymer and having an antibacterial effect". In the same way, reference is sometimes made to an "antibacterial powder".

In the case of antibacterial chemical fibres, these can be made of biopolymers, for example, cellulosic chemical fibres; these chemical fibres are consequently manufactured from a biopolymer. They can be manufactured, for example, in the form of spun fibres, such as viscose spun fibres, or extrusion fibres. The antibacterial chemical fibres can, however, also be chemical fibres made of synthetic polymers that have a coating comprising a biopolymer with antibacterial effect.

An antibacterial effect comprises bacteriostatic (germ-inhibiting) and/or bactericide (germ-killing) effects.

On the basis of the fibrous or powdered biopolymer, such a vacuum cleaner filter bag can be manufactured in an ecologically harmless and simple manner. Antibacterial staple fibres can, for example, replace coniferous wood cellulose fibres that were present in a nonwoven for reasons of the filter (for example, the cellulose fibres in a high-capacity airlaid layer in EP 0 960 645) and additionally take over the antibacterial equipping of the filter bag. In this way, the desired effect is achieved in an economical and ecological manner.

In addition, the disposal also does not present a problem because of the biodegradability of the biopolymers. Furthermore, biopolymers are also non-toxic, so that no risk is presented in the event of a burst vacuum cleaner filter bag or the disposal of a vacuum cleaner filter bag from which a portion of the biopolymer material might escape. Some biopolymers additionally have the advantage that they show a fungicidal and/or antiviral effect, in addition to an antibacterial effect.

Because individual fibres, and so not complete plant parts, are used, filter media can be manufactured in accordance with the conventional nonwoven folding method. Staple fibres in various lengths and counts are available on the market (for example, from SWICOFIL AG Textile Services, Switzerland).

A vacuum cleaner filter bag normally comprises a bag wall made of a filter material, i.e., made of a material that is air-permeable. A hollow space is delimited by this bag wall, whereby an airflow that transports dust particles is conducted into this hollow space. For this purpose, the bag wall has an inlet opening, whereby a securing plate is also often attached to the exterior side of the bag wall in the vicinity of this inlet opening, in order to fix the vacuum cleaner filter bag in place in a vacuum cleaner with this securing plate.

The biopolymer of the antibacterial fibres or of the powder can be chitosan and/or cellulose (pulp) from bamboo.

Both materials have the advantage that it is possible to manufacture from them, in particular, fibres with antibacterial characteristics in a simple manner. If cellulose is obtained from bamboo, the antibacterial substance "bamboo kun" is bound to the cellulose polymer. This active substance is bound so solidly to the cellulose polymers that the antibacterial effect is even retained in the event of further processing into staple fibres or textiles and repeated washing.

Because of its positive Charge, chitosan powder can be advantageously electrostatically bound to electrostatically charged fibres. In addition, chitosan in particular also has a fungicidal and antiviral effect. Chitosan can have different chain lengths, which can be selected according to the requirements, for example, in order to obtain a water-soluble form. The solubility of chitosan in diverse solvents additionally allows processing in the so-called electrospun nonwoven method (see W. Albrecht et al., *Nonwoven Fabrics*, Wiley-VCH, 2000) or the atomization of an aqueous chitosan solution.

Attention is drawn to the fact that the biopolymer can also have a source other than bamboo or chitosan, as long as the resulting fibres or the resulting powder has an antibacterial or fungicidal effect.

In the case of the previously described vacuum cleaner filter bags, the antibacterial fibres can particularly be formed as bamboo pulp fibres, bamboo staple fibres and/or chitosan fibres.

Bamboo pulp fibres are plant fibres and can particularly be manufactured from bamboo cellulose (bamboo pulp) by means of a hammer mill or by dispersion in water (and subsequent further processing in the wetlaying method). Bamboo staple fibres are cellulosic chemical fibres and, like coniferous wood cellulose, can be spun from solutions of cellulose or cellulose derivatives, for example by means of a viscose process. A possible manufacturing method is, for example, described in JP 2005-126871. The case of the chitosan fibres can, in particular, involve spun chitosan fibres, for example chitosan fibres•electrospun or spun according to the viscose method. Viscose and electrospun nonwoven methods are, for example, described in W. Albrecht et al., Nonwoven Fabrics, Wiley-VCH, 2000. The chitosan fibres can be formed as staple fibres or as continuous fibres.

In the case of the abovementioned vacuum cleaner filter bags, the powder can be bamboo pulp powder and/or chitosan powder. The former can be obtained, for example, by grinding bamboo pulp.

The bag wall of the previously mentioned vacuum cleaner filter bag can have at least one filter material layer, which comprises the antibacterial fibres.

The bag wall of a vacuum cleaner filter bag can generally comprise one or more filter material layers. By using antibacterial biopolymer fibres in a filter material layer, their effect is particularly exerted on the bacteria that penetrate into the bag wall. A further advantage lies in the fact that the antibacterial fibres are not released, or are released only to a small extent, should the vacuum cleaner filter bag burst.

The at least one filter material layer can comprise the antibacterial fibres in more than 5 wt. %, in particular more than 10 wt. %, in particular more than 20 wt. %. With such a proportion of antibacterial fibres in the at least one filter material layer, an advantageous antibacterial effect is achieved. If the fibres with antibacterial effect do not make up 100 wt. % of the filter material layer, the remaining fibres can be natural and/or chemical fibres.

The at least one filter material layer can be arranged in the air flow direction at the most upstream point, at the most downstream point and/or between two additional filter material layers.

The at least one filter material layer can consequently be appropriately positioned depending on the preferred application. In the case of a positioning arranged at the most upstream point, the at least one filter material layer consequently forms the inner layer of the vacuum cleaner filter bag.

The bag wall of the previously described vacuum cleaner filter bag can comprise at least two additional filter material layers, between which the antibacterial fibres are arranged. In this case, the antibacterial fibres can be provided, in particular, loosely, meaning, in particular, not bound, between the two additional filter material layers.

For example, during the manufacture of the filter structure, a first of the two additional filter material layers can be provided on which the material comprising the biopolymer is then placed in a loose form (e.g., as loose staple fibres). The second of the two additional filter material layers can subsequently be placed in position. After this, the two additional filter material layers can be bonded to each other with the material arranged in between. In this way, particularly simple manufacture of the vacuum cleaner filter bag is possible.

The antibacterial fibres can be bonded to at least one of the two additional filter material layers, in particular, mechanically, chemically and/or thermally.

In the case of the previously described vacuum cleaner filter bags, the at least one filter material layer and/or at least one of the two additional filter material layers can be a filter paper layer, a drylaid nonwoven layer, particularly a carded or airlaid nonwoven layer, a wetlaid nonwoven layer or an extrusion nonwoven layer, particularly a meltblown layer, a spunbond layer or an electrospun nonwoven layer.

The term nonwoven is used in accordance with the definition given in ISO standard ISO 9092: 1988 or CEN Standard EN 29092. A nonwoven can, in particular, be a wetlaid or drylaid nonwoven or an extrusion nonwoven, particularly a meltblown (meltspun microfibre nonwoven) or spunbond (filament spun nonwoven). The distinction between wetlaid nonwovens and conventional wetlaid paper is made in accordance with the abovementioned definition as it is also used by the International Association Serving the Nonwovens and Related Industries EDANA (www.edana.org). Whenever the term paper or filter paper is mentioned, (conventional) wetlaid paper that is included in the above-mentioned definition of nonwoven is meant.

A drylaid or wetlaid nonwoven layer or a filter paper layer can, in particular, comprise bamboo pulp fibres, bamboo staple fibres and/or chitosan staple fibres. In addition to these fibres, such a paper layer or nonwoven layer can also comprise further cellulose fibres and/or staple fibres. If a wetlaid paper layer or nonwoven layer comprises chitosan staple fibres, it also still comprises cellulose fibres and/or cellulose staple fibres (for example, produced from coniferous wood), in order to make it possible to form hydrogen bridges.

In particular, the above-described vacuum cleaner filter bag can have at least one drylaid or wetlaid nonwoven layer that contains bamboo staple fibres, bamboo pulp fibres and/or chitosan fibres, particularly with a proportion of more than 5 wt. % to 100 wt %. A corresponding drylaid nonwoven layer can particularly be carded or airlaid.

The spunbond layer (layer of filament-spun nonwoven) can particularly be compacted by means of a thermal embossing calendar. The spunbond layer can be formed as a microdenier spunbond layer. Spunbond layers of this type, as described in EP 0 960 645, for example, preferably have an average fibre diameter of less than 12 µm.

As an alternative or in addition to the use of antibacterial fibres made from a biopolymer, the filter material layer can be one of the above-mentioned nonwoven layers or a filter paper layer, whereby at least a portion of the fibres, particularly all fibres, are coated with a biopolymer with antibacterial effect. For this purpose, a nonwoven layer can, for example, be sprayed with water in which chitosan of a suitable chain length is dissolved, and then dried; according to a further example, in the case of an extrusion nonwoven, particularly a meltblown, the polymer can, when exiting the spinneret, be quenched with a water spray in which chitosan is dissolved, so that a coating of the fibres with chitosan is obtained.

In the case of coated fibres, the fibres can be natural and/or chemical fibres. The fibres can involve both staple fibres and continuous fibres. For example, cellulose fibres and/or fibres comprising one or more polyolefins, such as polyethylene (PE) or polypropylene (PP), are possible. During the bonding to polyolefins, it can be advantageous to electrostatically load the filaments or the staple fibres before the coating. This can take place by means of triboelectric charging (in the case of staple fibres) or corona charging (in the case of an extrusion nonwoven).

The at least one filter material layer and/or at least one of the two additional filter material layers can be arranged upstream, particularly immediately upstream, of a filter paper layer, a drylaid nonwoven layer, in particular a carded or airlaid nonwoven layer, a wetlaid nonwoven layer or an extrusion nonwoven layer, in particular a meltblown layer, a spunbond layer or an electrospun nonwoven layer.

Again, here and in the following the terms "upstream" and "downstream" refer to the air flow direction during the operation of the vacuum cleaner filter bag. The filter material layer facing the interior of the vacuum cleaner filter bag is consequently the layer arranged at the most upstream point. One layer is arranged directly upstream of another layer if no further filter material is arranged between the two layers; it is possible that there is only an adhesive located between the two layers.

Alternatively or additionally, the at least one filter material layer and/or at least one of the two additional filter material layers can be arranged downstream, particularly immediately downstream, of a filter paper layer, a drylaid nonwoven layer, in particular a carded or airlaid nonwoven layer, a wetlaid nonwoven layer or an extrusion nonwoven layer, in particular a meltblown layer, a spunbond layer or an electrospun nonwoven layer.

Possible filter structures or superstructures of the bag wall are described, for example, in EP 0 960 645. With reference to this patent, it is possible, for example, for the high-capacity layers, fine filter layers and/or support layers mentioned there to comprise antibacterial fibres. Alternatively or additionally, a filter material layer with the antibacterial fibres can also be provided in the direction of flow before and/or after one of these layers.

The at least one filter material layer of the described vacuum cleaner filter bag can be thermally, mechanically and/or chemically compacted.

In the case of the previously indicated vacuum cleaner filter bag, the at least one filter material layer can cover the surface of the bag wall either only partially or completely. In the case of only partial covering, the at least one filter material layer can, in particular, be arranged in an area in which an airflow entering into the vacuum cleaner filter bag appears on the interior side of the bag wall.

The antibacterial fibres and/or the antibacterial powder can have the biopolymer with a proportion of at least 5 wt. %, particularly at least 10 wt. %, particularly at least 20 wt. %. The antibacterial fibres can, for example, be formed as cellulose fibres or continuous fibres. The continuous fibres can, particularly in the case of electrospun fibres, have an average fibre diameter of less than 1 µm, preferably less than 0.5 µm.

Alternatively, the antibacterial fibres can be formed as staple fibres. The staple fibres can thereby have a count of 1-10 dtex, particularly 1-6 dtex, and/or an average fibre length of 20 to 200 mm, particularly 30 to 80 mm.

The antibacterial powder can, in particular, be bound to fibres. The fibres can be natural and/or chemical fibres. The fibres can be either staple fibres or continuous fibres. For example, cellulose nores and/or nores comprising one or more polyolefins, such as polyethylene (PE) or polypropylene (PP), are possible. The fibres can, in particular, be electrostatically charged split fibres. The biopolymer can be electrostatically bound to the fibres.

The invention furthermore provides a vacuum cleaner filter bag, particularly as previously described, with a securing plate, comprising a biopolymer and having an antibacterial effect. This allows hygienic removal of the vacuum cleaner filter bag from the vacuum cleaner after the use of the vacuum cleaner filter bag.

The biopolymer can be incorporated into the securing plate and/or bound to the surface. For example, the material of the securing plate can contain chitosan powder.

In the case of the previously described vacuum cleaner filter bag, the securing plate can comprise a plastic. Chitosan powder, for example, can be incorporated into the plastic. In the case of an injection-moulded securing plate, this can be achieved in accordance with all customary methods with which, for example, glass fibres or talcum are also incorporated into injection-moulded parts.

The invention furthermore provides a vacuum cleaner with a dust collection area for holding a vacuum cleaner filter bag, whereby the wall of the dust collection area comprises at least partially a material, comprising a biopolymer, with an antibacterial effect.

Understood as the dust collection area is the hollow space in a vacuum cleaner housing into which the vacuum cleaner filter bag is inserted for operation or in which the dust is intercepted, in the case of a vacuum cleaner that, for example, works on the cyclotron principle.

The vacuum cleaner can alternatively or additionally have a suction pipe and/or a connection conduit between the suction pipe and the vacuum cleaner area, whereby the wall of the suction pipe and/or of the connection conduit comprises at least partially a material comprising a biopolymer and having an antibacterial effect.

The material comprising the wall can, in particular, be a plastic. The biopolymer, in particular, chitosan powder, can be incorporated into the wall and/or bound to the surface.

The invention additionally provides a method for manufacturing a filter material layer for a vacuum cleaner filter bag with the steps:

Extrusion of polymer material through a multiple number of spinnerets,

Quenching of the extruded polymer material with a water spray, whereby the water spray contains a biopolymer, Lay-up of the quenched polymer material, in order to form a nonwoven layer.

This facilitates an antibacterial coating of chemical fibres in a simple manner.

The extrusion step can, in particular, comprise an extrusion in accordance with the meltblown method.

It can thereby particularly involve a method for manufacturing a meltblown layer. The biopolymer can, in particular, be chitosan, which can, in particular, be dissolved in water. The water spray for quenching preferably has an average drop size of from 1 to 10 μm. Because the water spray is used for quenching, meaning that it is sprayed on to the still-hot extruded polymer, the latter is sprayed on close to the spinneret. The polymer can, for example, be polyethylene or polypropylene.

BRIEF DESCRIPTION OF THE DRAWINGS

Further characteristics and advantages of the invention are explained in the following on the basis of examples and the figures. Schematically shown are.

DETAILED DESCRIPTION

Figure 1:
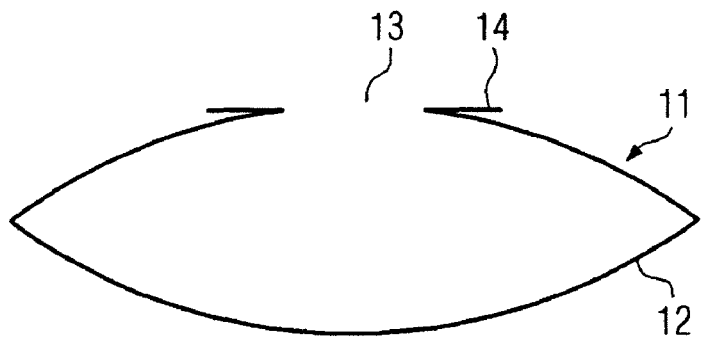
FIG. 1 a cross-section through an example of a vacuum cleaner filter bag according to the invention.

FIG. 1 schematically illustrates the cross-sectional view of an example of a vacuum cleaner filter bag 11. The vacuum cleaner filter bag 11 has a bag wall 12, which is formed by means of air-permeable filter material.

During the operation of such a vacuum cleaner filter bag, air that is suctioned in and that carries with it dust particles, bacteria, etc., flows through an inlet opening 13 and into the interior of the vacuum cleaner filter bag 11. A portion of the suctioned-in particles, bacteria, etc., remain in the interior of the bag, while another portion penetrates into the bag wall 12, where it is held in the pores.

A securing plate is attached to the bag wall in the area of the inlet opening 13. The securing plate can, for example, be made of cardboard or a plastic. The attachment of the securing plate to the bag wall can, for example, take place by means of an adhesive or ultrasonic welding.

The securing plate 14 can already be antibacterially equipped. For this purpose, it can, in particular, comprise a plastic into which chitosan powder is incorporated. The antibacterial effect is achieved by chitosan pellets located on the surface of the securing plate.

In this connection, attention is drawn to the fact that alternatively or additionally, the wall of the dust collection area of a vacuum cleaner in which a vacuum cleaner filter bag of this type is arranged, and/or the wall of a feeding vacuum cleaner pipe can comprise a plastic, for example, with chitosan powder.

The bag wall 12 of the vacuum cleaner filter bag 11 consists of one or more filter material layers, which are arranged to some extent loosely and to some extent connected to one another. The connection of the filter material layers can take place, for example, via an adhesive, e.g., hot-melt, or ultrasonic welding, depending on the type of layer and the material used.

Examples of possible filter structures for building up a bag wall 12 are schematically illustrated in FIGS. 2 to 6. The airflow direction (from the bag interior outwards) is indicated in these figures with arrows.

Figure 2:
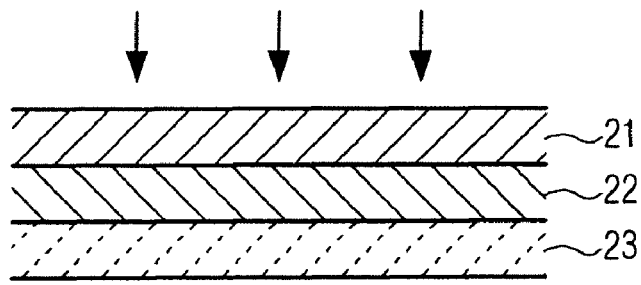
FIGS. 2 to 6 the configuration of examples of a filter structure of a vacuum cleaner filter bag, as shown, for example, in FIG. 1, in a cross-sectional view.

FIG. 2 shows a three-layer structure, whereby the layer 21, arranged at the most upstream point, is a wetlaid nonwoven layer. This wetlaid nonwoven layer comprises bamboo staple fibres that are manufactured from bamboo pulp. This wetlaid layer can comprise up to 100 wt. % bamboo staple fibres. In order to increase the pore volume and the dust-holding capacity, however, the wetlaid layer preferably comprises up to 40 wt. % chemical fibres, for example, polyester staple fibres.

The wetlaid nonwoven layer can have a gram weight of from 20 to 200 $g/m^2$, preferably 50 to 100 $g/m^2$. The air permeability of the wetlaid nonwoven layer can be between 500 and 8,000 $l/(m^2 s)$, preferably 2,000 to 4,000 $l/(m^2 s)$.

Due to the bamboo staple fibres, this wetlaid layer has antibacterial, in particular, bacteriostatic and bactericidal, characteristics. The bamboo staple fibres thereby work particularly on germs that lie on the nonwoven layer or have penetrated into it and become incorporated in it. Instead of the bamboo staple fibres, bamboo pulp fibres, for example, can also be used.

The following layer 22 is a meltblown nonwoven layer. This meltblown layer can, in particular, be manufactured from polypropylene continuous fibres. The meltblown layer can be formed in such a way that its filter-characteristics correspond to a so-called filtration grade meltblown, as is described in EP 0 960 645. This nonwoven layer consequently takes on the function of a fine filter layer.

A spunbond layer 23 is provided downstream, which spunbond layer functions, in particular, as a support nonwoven for the filter configuration. The spunbond layer can, in particular, be formed in such a way that it corresponds to a so-called microdenier spunbond nonwoven layer in accordance with EP 0 960 645.

Figure 3:
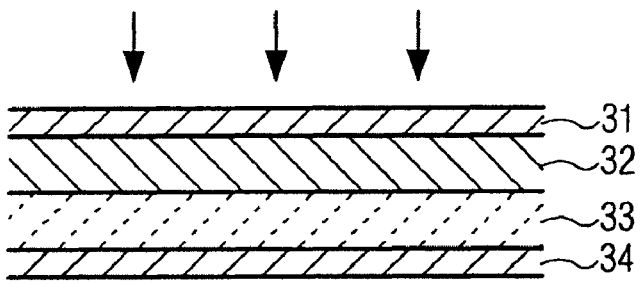

FIG. 3 shows a four-layer configuration in which the two exterior layers 31 and 34 are formed as spunbond layers. These two layers can also particularly correspond to a microdenier spunbond nonwoven layer in accordance with EP 0 960 645. Layers 31 and 34 do not have to be identical, however.

A meltblown nonwoven layer 32 follows as the second layer in the airflow direction. This meltblown layer can, in principle, be formed in such a way that it corresponds to a so-called high-bulk meltblown in accordance with EP 0 960 645. In the present case, however, the meltblown fibres are coated with chitosan. This was achieved by means of quenching the extruded polymer with water spray (water quenching) during the meltblown manufacture, whereby chitosan, in a water-soluble form, was added to the water. The chitosan is then bound to the meltblown filaments, consequently achieving the antibacterial effect in this nonwoven layer.

The next-to-last layer in the flow direction is, in turn, a meltblown nonwoven layer 33, which is formed, however, as a fine filter layer, as is the layer 22 in FIG. 2. The filaments of the layer 33 can also be coated with chitosan, analogously to the layer 32.

Figure 4:
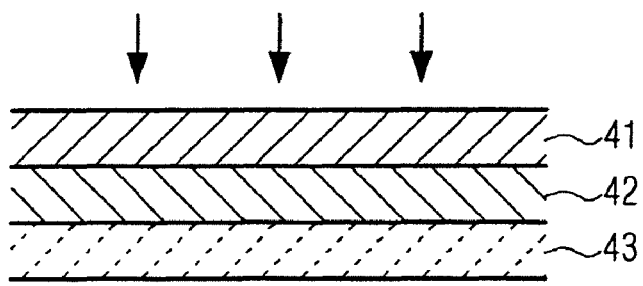

FIG. 4 shows the interior layer 41 as a drylaid nonwoven layer. This nonwoven layer can, in particular, be carded or airlaid. Bamboo pulp fibres, bamboo staple fibres and/or chitosan fibres are used as staple fibres. This drylaid nonwoven layer can, in particular, be formed in such a way that its filtration characteristics correspond to those of a drylaid high-capacity paper in accordance with EP 0 960 645, whereby the natural fibres in the present case are formed by the bamboo fibres and/or the chitosan fibres. Compaction of this nonwoven layer can, for example, take place with the help of a latex binder or in a thermal manner with the use of binder fibres. In this connection, attention is drawn to the fact that a "high-capacity paper" in EP 0 960 645 is a nonwoven in the sense of the definition mentioned at the beginning, and is not a conventional paper.

The layer 41 is followed in the flow direction by a meltblown nonwoven layer 42, which can, for example, correspond to the fine filter layer 33 in FIG. 3.

The outermost layer 43 is a wetlaid filter paper layer, and so not a nonwoven layer. This filter paper layer essentially fulfils the function of a support layer. For example, it can have a gram weight of 50 g/m$^2$ and air permeability of 200 to 500 l/(m$^2$s). It typically has a proportion of cellulosic fibres amounting to more than 90%. The cellulosic fibres can be cellulose fibres or staple fibres, whose origin is, for example, coniferous wood or also, if an antibacterial effect is to be achieved, bamboo.

Figure 5:
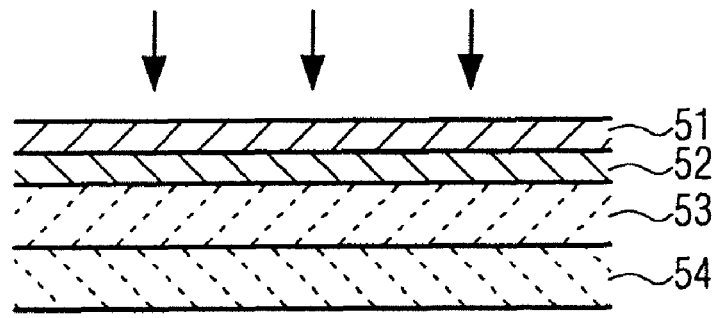

FIG. 5 likewise shows an example of a filter structure. The innermost layer 51 is a spunbond nonwoven layer, which can correspond, in particular, to the layer 23 in FIG. 2. The outermost layer 54 is, as in FIG. 4, a wetlaid filter paper.

A meltblown nonwoven layer 53 comes before the filter paper 54. In the manufacture of a vacuum cleaner filter bag of this type, loose fibres are positioned on the meltblown layer 53, whereby a layer 52 is formed from these loose fibres after the completion of the bag wall. These loose fibres can, in particular, be chitosan fibres, bamboo pulp fibres and/or bamboo staple fibres.

After the application of the spunbond layer 51, the filter material layers are connected to one another by means of ultrasonic welding. Alternatively, it is also possible to spray a hot-melt on to the loose fibres before the application of the spunbond overlay 51, so that then conglutination of the fibres with the meltblown layer 53 and the spunbond layer 51 takes place.

Figure 6:
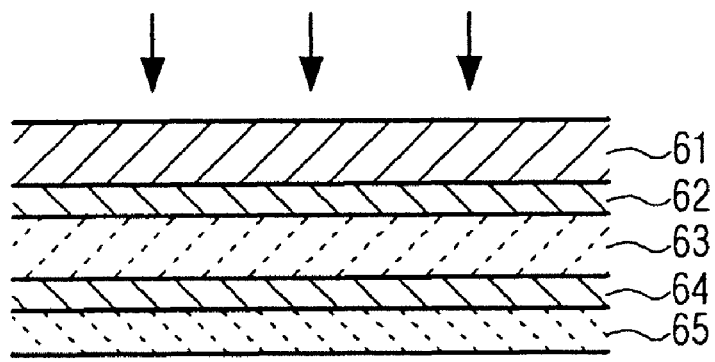

A further example is schematically illustrated in FIG. 6. Here the approach side of the bag wall is formed by a drylaid nonwoven layer 61, which corresponds to the layer 41 in FIG. 4. This drylaid nonwoven layer 61 is followed by a layer of electrospun chitosan continuous fibres, such as are described in D. Vu, *Electrospinning of Oriented and Non-oriented Ultrafine Fibers of Biopolymers*, Dissertation, University of Nebraska-Lincoln, 2005.

Following the chitosan layer 62 is a meltblown layer 63, which is formed as a fine filter layer corresponding to layer 42. The meltblown layer 63 is, in turn, followed by an electrospun chitosan layer 64, which can be manufactured in a manner similar to that for layer 62, but which does not have to be identical to this layer 62.

A spunbond layer 65 is provided on the downstream side, which spunbond layer, in turn, primarily has the function of a support layer.

Further modifications are, however, possible in the examples shown in FIGS. 2 to 6. For example, the various filter material layers can also be combined with one another in another form, additional layers can be added and individual layers can also be left out. Furthermore, the materials mentioned can also be combined with one another in another form, or replaced with other materials.

Even should EP 0 960 645 be referenced in connection with the individual layers in FIGS. 2-6, this should be seen only as by way of example. The respective nonwoven layers and/or filter paper layers can also be manufactured in another manner and can have other filter characteristics.

Figure 7:
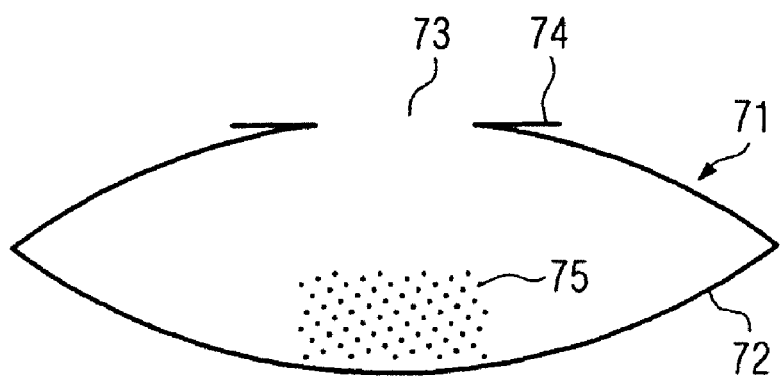
FIG. 7 a further example of a vacuum cleaner filter bag in a cross-sectional view.

FIG. 7 shows a schematic cross-sectional view of a vacuum cleaner filter bag 71, which has a bag wall 72 in which an inlet opening 73 is provided. In the area of the inlet opening 73 is arranged a securing plate 74, which can be formed in accordance with the securing plate 14 in FIG. 1.

The bag wall 72 can have a configuration such as illustrated in FIGS. 2 to 6. Alternatively, the bag wall in the example shown in FIG. 7 can, however, be built up from other filter material layers and from a different number of filter material layers. In particular, it is not necessary for any of the filter material layers to have a biopolymer with an antibacterial effect.

Loose antibacterial fibres 75 are provided for this purpose in the interior of the vacuum cleaner filter bag in the example shown in FIG. 7. These loose fibres here can, for example, be chitosan fibres, bamboo pulp fibres and/or bamboo staple fibres. These staple fibres can be introduced into the vacuum cleaner filter bag 71 in such a manner that they move freely. Alternatively, an antibacterial powder, for example, ground bamboo pulp, or split fibres coated with chitosan powder or bamboo pulp powder can also be provided.

Alternatively, the antibacterial fibres or the antibacterial powder can also initially be present in a casing, which is destroyed during the operation of the vacuum cleaner filter bag in the presence of a predetermined volumetric flow rate, so that the fibres or the powder is released. A corresponding formation of the casing is described, for example, in WO 2005/060807.

The invention claimed is:

1. A vacuum cleaner filter bag comprising:
an interior of the vacuum cleaner filter bag; and
a bag wall comprising a filter material; wherein (a) the interior of the vacuum cleaner filter bag or (b) the bag wall or (c) both the interior of the vacuum cleaner filter bag and the bag wall comprise fibers made of a biopolymer, the biopolymer itself having an antibacterial effect, the fibers comprise at least one of bamboo pulp fibers, bamboo staple fibers and chitosan fibers;
wherein in (b) or (c) the bag wall comprises at least one nonwoven layer comprising the antibacterial fibers or the bag wall comprises at least two nonwoven layers between which the antibacterial fibers are arranged;
wherein the at least one or the at least two nonwoven layers are a drylaid nonwoven layer, a wetlaid nonwoven layer or an extrusion nonwoven layer.

2. The vacuum cleaner filter bag according to claim 1, comprising a powder provided in the interior of the vacuum cleaner bag or in the bag wall or in both the interior of the vacuum cleaner filter bag and the bag wall the powder produced from a biopolymer with an antibacterial or fungicidal effect or both an antibacterial and fungicidal effect.

3. The vacuum cleaner filter bag according to claim 2, wherein the powder biopolymer is chitosan or cellulose or both chitosan and cellulose made from bamboo.

4. The vacuum cleaner filter bag according to claim 2, wherein the powder comprises the powder biopolymer with a proportion of at least 5 wt %.

5. The vacuum cleaner filter bag according to claim 2, wherein the powder is bound to the fibers.

6. The vacuum cleaner filter bag according to claim 5, wherein the fibers comprise natural or chemical fibers.

7. The vacuum cleaner filter bag according to claim 5, wherein the powder is electrostatically bound to the fibers.

8. The vacuum cleaner filter bag according to claim 1, wherein the bag wall has at least one filter material layer comprising the antibacterial fibers, and wherein the at least one filter material layer comprises antibacterial fibers in more than 5 wt. %.

9. The vacuum cleaner filter bag according to claim 1, wherein the at least one nonwoven layer is arranged in an air flow direction at one of a most upstream point, a most downstream point, and between two additional filter material layers.

10. The vacuum cleaner filter bag according to claim 1, wherein the at least one or the at least two nonwoven layers are arranged downstream, of a filter paper layer, a drylaid nonwoven layer, a wetlaid nonwoven layer or an extrusion nonwoven layer.

11. The vacuum cleaner filter bag according to claim 1, wherein the bag wall has at least one filter material layer comprising compacted antibacterial fibers, and wherein the at least one filter material layer is compacted thermally, mechanically or chemically or by a combination of these types of compaction.

12. The vacuum cleaner filter bag according to claim 1, wherein the bag wall has at least one filter material layer comprising antibacterial fibers, and wherein the at least one filter material layer covers a surface of the bag wall either only partially or completely.

13. The vacuum cleaner filter bag according to claim 1, wherein the antibacterial fibers comprise a biopolymer with a proportion of at least 5 wt. %.

14. The vacuum cleaner filter bag according to claim 1, comprising a securing plate comprising a biopolymer and having an antibacterial effect.

15. The vacuum cleaner filter bag according to claim 14, wherein the biopolymer of the securing plate is incorporated into the securing plate or bound to the surface.

16. The vacuum cleaner filter bag according to claim 14, wherein the securing plate comprises a plastic.

17. The vacuum cleaner filter bag according to claim 1, wherein the fibers comprise chitosan or cellulose or both chitosan and cellulose made from bamboo.

18. The vacuum cleaner filter bag according to claim 1, wherein the antibacterial fibers comprise cellulose fibers or continuous fibers.

19. The vacuum cleaner filter bag according to claim 1, wherein the antibacterial fibers comprise staple fibers.

20. The vacuum cleaner filter bag according to claim 19, wherein the staple fibers have a count of 1-10 dtex, or an average fiber length of 20 to 200 mm, or both a count 1-10 dtex, and an average fiber length of 20 to 200 mm.

21. A vacuum cleaner filter bag comprising:
an interior of the vacuum cleaner filter bag; and
a bag wall comprising a filter material; wherein the bag wall comprises fibers made of a biopolymer, the biopolymer itself having an antibacterial effect, the fibers comprise at least one of bamboo pulp fibers, bamboo staple fibers and chitosan fibers;
wherein the bag wall comprises at least one nonwoven layer comprising the antibacterial fibers or the bag wall comprises at least two nonwoven layers between which the antibacterial fibers are arranged;
wherein the at least one or the at least two nonwoven layers are a drylaid nonwoven layer, a wetlaid nonwoven layer or an extrusion nonwoven layer.

22. The vacuum cleaner filter bag according to claim 21, wherein the bag wall and an interior of the vacuum cleaner filter bag both comprise fibers made of the biopolymer.

* * * * *